United States Patent
Koblischke et al.

(10) Patent No.: US 9,489,485 B2
(45) Date of Patent: Nov. 8, 2016

(54) SYSTEM FOR MANAGING AND ANALYZING METABOLIC PATHWAY DATA

(75) Inventors: Carsten Koblischke, Lohmar-Honrath (DE); Markus Hemmer, Meckenheim (DE)

(73) Assignee: Waters GmbH, Eschborn (DE)

( * ) Notice: Subject to any disclaimer, the term of this patent is extended or adjusted under 35 U.S.C. 154(b) by 1033 days.

(21) Appl. No.: 12/302,309

(22) PCT Filed: Jun. 6, 2007

(86) PCT No.: PCT/EP2007/005033
§ 371 (c)(1),
(2), (4) Date: Jul. 31, 2009

(87) PCT Pub. No.: WO2007/141016
PCT Pub. Date: Dec. 13, 2007

(65) Prior Publication Data
US 2009/0307309 A1   Dec. 10, 2009

(30) Foreign Application Priority Data

Jun. 6, 2006   (EP) ..................... 06011659

(51) Int. Cl.
*G06F 15/16* (2006.01)
*G06F 19/12* (2011.01)
(Continued)

(52) U.S. Cl.
CPC ............... *G06F 19/12* (2013.01); *G06F 9/465* (2013.01); *G06F 17/509* (2013.01); *G06F 19/00* (2013.01); *G06F 19/10* (2013.01); *G06F 19/70* (2013.01)

(58) Field of Classification Search
CPC . H04L 67/42; H04L 29/06047; H04L 41/00; H04L 41/22; H04L 51/046; H04L 51/066; G06F 19/12; G06F 19/10; G06F 19/00; G06F 9/465; G06F 19/70; G06F 17/509
USPC ........ 709/203, 201, 220–222, 227, 228, 238
See application file for complete search history.

(56) References Cited

U.S. PATENT DOCUMENTS 5,930,154 A   7/1999   Thalhammer-Reyero
6,119,122 A * 9/2000   Bunnell
(Continued)

FOREIGN PATENT DOCUMENTS

EP   1628229   2/2006
WO   02/44992   6/2002

OTHER PUBLICATIONS

Salamonsen, W. et al; "BioJAKE"; A Tool for the Creation, Visualization and Manipulation of Metabolic Pathways; Proceedings of the Pacific Symposium on Biocomputing, (Jan. 4, 1999), pp. 392-400.

(Continued)

*Primary Examiner* — Kenneth R Coulter
(74) *Attorney, Agent, or Firm* — Waters Technologies Corporation

(57) ABSTRACT

A metabolic pathway data management and analysis system in a distributed communication network is provided comprising at least one application server running a metabolic pathway data management server application, at least one client workstation running a metabolic pathway data management client application in communication with the at least one application server via the distributed communication network, and at least one database for storing data in communication with the at least one application server via the distributed communication network, wherein said metabolic pathway data management client application provides a graphical user interface comprising a study editor and a pathway editor.

21 Claims, 13 Drawing Sheets

(51) Int. Cl.
    *G06F 9/46*       (2006.01)
    *G06F 17/50*     (2006.01)
    *G06F 19/00*     (2011.01)
    *G06F 19/10*     (2011.01)

(56) References Cited

U.S. PATENT DOCUMENTS

| | | | | |
|---|---|---|---|---|
| 2002/0145742 | A1* | 10/2002 | Koenig et al. | 358/1.1 |
| 2002/0156756 | A1* | 10/2002 | Stanley et al. | 706/47 |
| 2003/0225597 | A1* | 12/2003 | Levine | 705/3 |
| 2004/0249791 | A1* | 12/2004 | Waters et al. | 707/3 |
| 2005/0114398 | A1 | 5/2005 | Naik et al. | |
| 2005/0240352 | A1* | 10/2005 | Liang | 702/19 |
| 2005/0283347 | A1* | 12/2005 | Kimura et al. | 703/11 |
| 2007/0130133 | A1* | 6/2007 | Lee et al. | 707/4 |
| 2007/0219768 | A1* | 9/2007 | Ekins | G06F 19/704 703/11 |
| 2010/0250218 | A1* | 9/2010 | Ekins | G06F 19/704 703/11 |
| 2012/0029896 | A1* | 2/2012 | Ekins | G06F 19/704 703/11 |

OTHER PUBLICATIONS

Holford et al; "VitaPad: visualization tools for the analysis of pathway data", Bioinformatics. Apr. 15, 2005;21(8): 1596-602. Epup Nov. 25, 2004.

Chung et al; "ArrayXPath: Mapping and visualizing microarray gene-expression data with integrated biological pathway resources using Scalable Vector Graphics"; Nucleic Acids Res. Jul. 1, 2004;32 (Web Server issue): W460-4.

EECS and Genetics Departments, CWRU, Jul. 10, 2004, Version 2.0, Report 13, Division of Computer Science; Pathway Viewer Tool User Manual, Center for Computation Genomics.

Aitken et al.; "CoBrA: a bio-ontology editor"; Bioinformatics. Mar. 21, 2005, (6):vol. 21 825-6. Epub Oct. 28, 2004.

Talbott et al; "Adampting the Electronic Laboratory Notebook for the Semantic Era"; Proceedings of the 2005 International Symposium on Collaborative Technologies and Systems, May 2005.

Pancerella et al; "Metadata in the collaboratory for multi-scale chemical science"; Proceedings of the 2003 international conference on Dublin Core and Metadata Applications.

European Office Action dated Feb. 13, 2009 for European Application No. 06011659.7, 7 pages.

* cited by examiner

SYSTEM FOR MANAGING AND ANALYZING METABOLIC PATHWAY DATA

CROSS REFERENCE TO RELATED APPLICATIONS

This application is the national stage of International Application No. PCT/US2007/069657, filed May 24, 2007 and designating the United States, which claims benefit of and priority to United Kingdom Patent Application 06011659.7, filed Jun. 6, 2006, the entire contents of which is hereby incorporated by reference in its entirety.

TECHNICAL FIELD OF THE INVENTION

The invention relates to a computer-implemented system for managing and analysing information and data about metabolic pathways. In particular the invention relates to a metabolic pathway data management and analysis system in a distributed communication network.

BACKGROUND OF THE INVENTION

Investigations of metabolic pathways cover a broad range of laboratory techniques. Lead drug substances are administered to different animals, humans, cell tissues and the like. The chemical metabolizing and physical pathways of detoxification or excretion of the drug in the organisms are observed by analyzing different types of samples (urine, plasma, tissues extractions). It is also common that the active substance is a metabolite of the administered drug. The samples are primarily analyzed by High Performance Liquid Chromatography-Mass Spectrometry systems dividing and purifying the sample fractions and providing information about the number and type of metabolites. Due to a lack of direct information about the molecular structure the metabolites are primarily characterized by mass differences and major ions, both derived from mass spectra. Since e.g. hydroxylation of a xenobiotic is a common starter for a detoxification process a mass difference of "+16" for example is likely to be assumed as an "—OH" added to the molecule, although the position of the group is not known at an early stage of a study. The drug under investigation can also be administered in a radio labeled form making the identification among similar organism immanent substances easier. For more detailed information about the molecule structures NMR measurements are performed. For localization of metabolites within organisms/organs also immuno staining techniques in tissue slices are used. The goal of such investigations is also to propose a pathway within the different organisms/conditions.

In order to gain insights into metabolic pathways means are important that allow the management and interpretation of the acquired genomic data. With the emergence of potentially very large datasets from high-throughput gene expression and proteomics experiments, there is a recognized need to relate such data to known networks of biochemical processes and interactions. In support of these activities, a well structured, yet flexible, system and method for managing and analyzing metabolic pathway data are required.

SUMMARY OF THE INVENTION

According to a first aspect of the invention a metabolic pathway data management system in a distributed communication network is provided comprising at least one application server running a metabolic pathway data management server application, at least one client workstation running a metabolic pathway data management client application in communication with the at least one application server via the distributed communication network, and at least one database for storing data in communication with the at least one application server via the distributed communication network, wherein said metabolic pathway data management client application provides a graphical user interface comprising a study editor and a pathway editor.

Further aspects of the invention are defined in the subclaims.

It should be appreciated that the present invention can be implemented and utilized in numerous ways, including without limitation as a process, an apparatus, a system, a device, a method for applications now known and later developed or a computer readable medium. The foregoing and other features and advantages of the embodiments of the present invention will be more readily apparent form the following detailed description which proceeds with reference to the accompanying drawings.

DETAILED DESCRIPTION OF THE INVENTION

System Architecture

Figure 1:
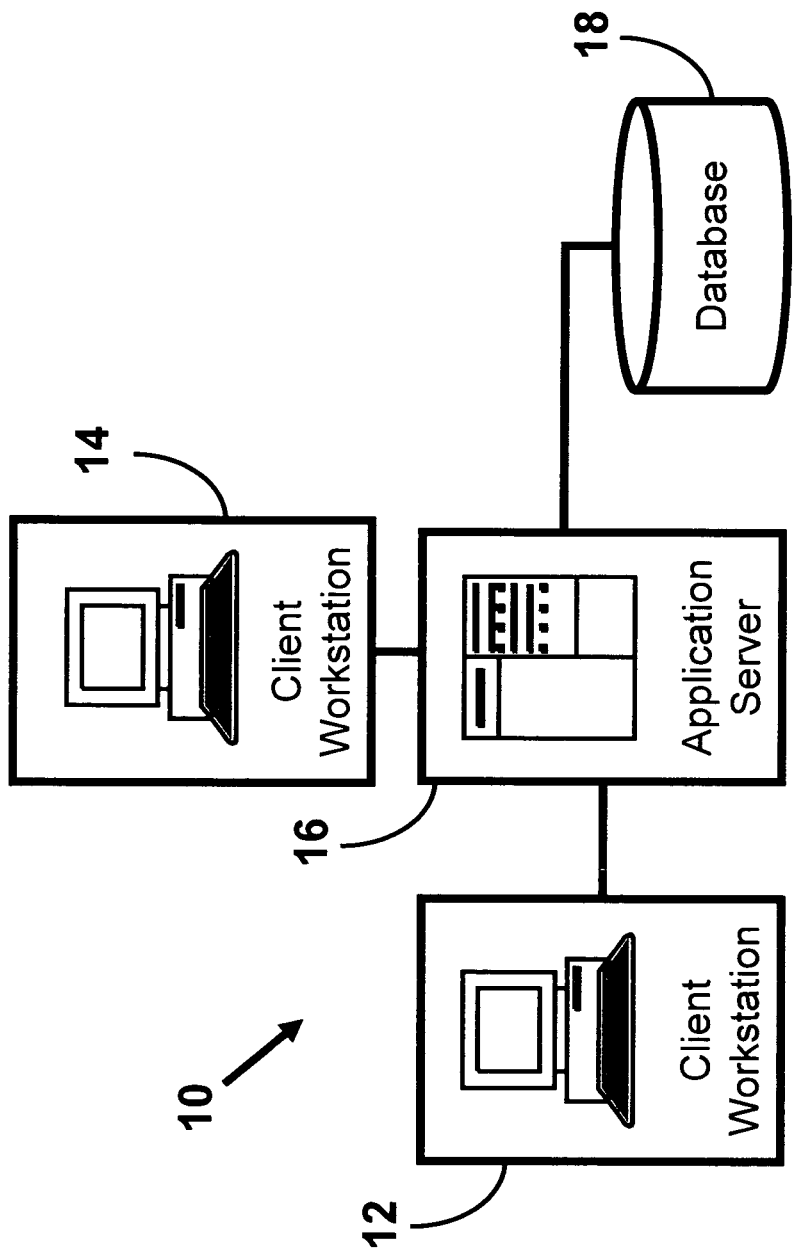
FIG. 1 shows schematically an exemplary network computer system for supporting a metabolic pathway data management system according to the present invention.

FIG. 1 illustrates an exemplary system 10 for supporting the metabolic pathway data management system (MPDMS) according to the present invention. Two exemplary client workstations 12, 14 are shown which may be connected via a distributed communication network or LAN to the application server 16 using any of a variety of methods known in the art. In this exemplary embodiment workstations 12, 14 are running a MPDMS client application and a MDPMS server application is running on the server 16. The LAN further includes a shared database 18 and optionally a long term data archive (not shown). Preferably, the shared database 18 is a multi-user, multi-view relational database such as an ORACLE database. The long term data archive is used to provide virtually unlimited amounts of "virtual" disk space, e.g., by means of a multi-layer hierarchical storage management system. However, the present invention is not limited to the illustrated embodiment and more or fewer and equivalent types of components can be used also as would be appreciated by those of ordinary skill in the art.

The different components of the system 10 described above, e.g., the client workstations 12 and 14, the application server 16, and the database 18 are preferably completely separated to allow conformity with company preferences, workloads, and infrastructure. This can be achieved by adhering to at least a 3-tier client-server architecture. Any suitable device connected to the LAN, e.g. a client workstation or an analytical instrument, should be able to interface via TCP/IP to the application sever 16, provided the appropriate client software has been installed and configured thereon. Optionally, multiple application servers can be provided which allow for data and metadata replication. Preferably, the system 10 allows the support of wireless environments, handheld and TabletPCs, Offline Clients, access via voice-control and the like.

The architecture of the system 10 readily allows the connection of several such LANs all over the world. This is particularly advantageous for globally operating companies that run several research laboratories in different countries and/or continents. Accordingly, all data and related metadata are immediately globally available. Search functions are available for all servers simultaneously.

Preferably the metabolic pathway data management system according to the present invention is embedded within or is configured to cooperate with an electronic laboratory notebook (ELN) application also implemented on the LAN 10, such as the ELN commercially available from Waters Corporation, Milford, Mass., USA, or as described in EP 04 024 280, which is incorporated herein by reference. Such an electronic laboratory notebook allows scientists of different research groups working together on a project to enter all type of data into a database. In addition to the data coming from instruments text, pathways, structures, tables and other data can be stored in the electronic laboratory notebook. The information can be updated and refined during the further investigation process. Scientific data such as chromatograms or spectra can be displayed within the electronic laboratory notebook and annotations can be made. The ELN provides the scientist with comprehensive search capabilities, and can act as an ELN knowledge base.

Figure 2:
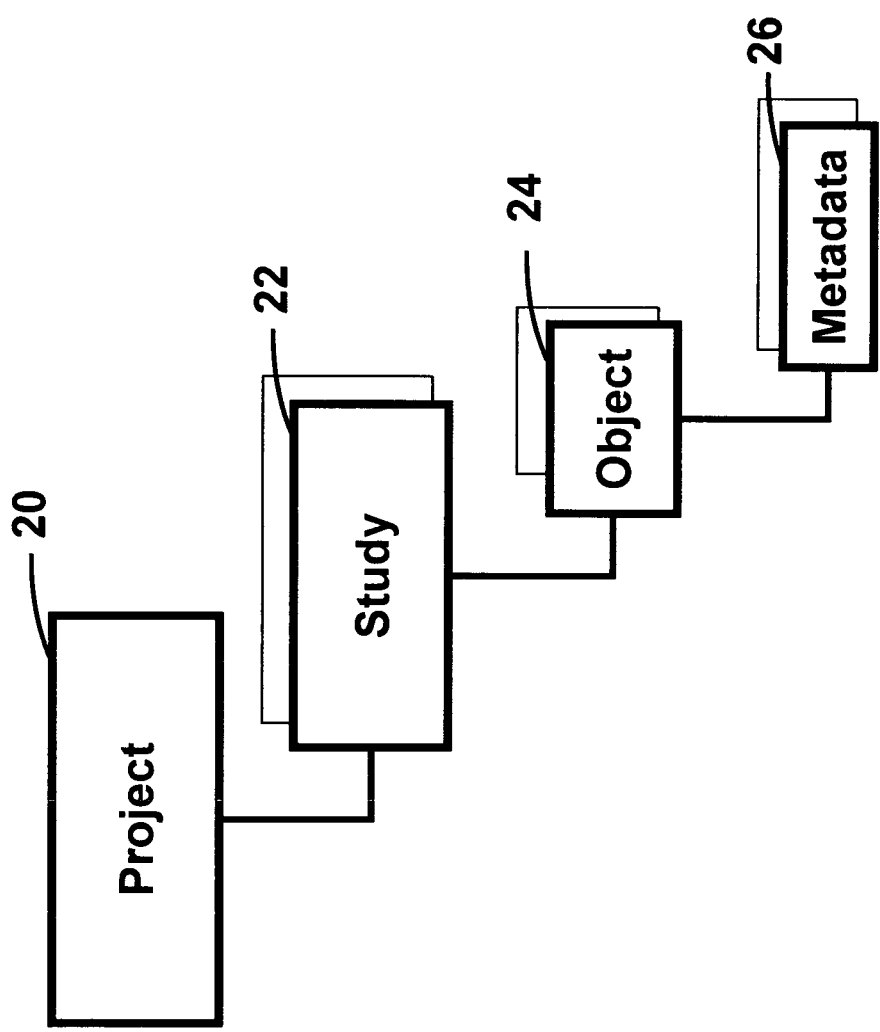
FIG. 2 shows schematically the different data types and their dependency provided by an exemplary metabolic pathway data management system according to the present invention.

Different types of data are produced in the course of the investigation of a metabolic pathway, such as instrument measurement data, data from scientific data processing applications, text from text processing applications, tabular data, images and so on. In order to achieve a straightforward categorization of data objects, according to the present invention metadata are used as classifiers. FIG. 2 shows the preferred data structure defined according to the present invention. A project 20 is a collection of different studies 22. A study 22 is a collection of information in a logical context. Studies 22 contain a series of different data objects or objects 24 containing information units, such as text, images, tables, graphs and the like. Finally, the "meaning" of data is provided by metadata 26 that describe the data and provide the context for its interpretation. Although the above "hierarchy of data" according to a preferred embodiment of the MDPMS according to the present invention is exemplary, it provides advantages in that the workflows in a laboratory are closely reflected.

Since the MPDMS database can hold all of the data mentioned above, an advantageous feature of the present invention is to provide means for structuring/categorizing data objects in a simple and preferably automatic way. The long time frame of a metabolic pathway study may result in a very large amount of data objects belonging to one study. Accordingly, there is a need for a flexible way to provide an overview of the contents of the study.

The MPDMS client application running on the client work stations 12, 14 provides a graphical user interface comprising preferably a study editor and a pathway editor, which will be described in more detail below. As will become clear to the person skilled in the art, the MPDMS server and client applications are advantageously realised by object-oriented programming techniques such as the C++ programming language. However, other programming languages can also be used.

The system according to the present invention includes a study editor module or study editor. The study editor is the main interface for the user, by means of which the user can store data objects in the database, navigate within data objects in the database, categorize data objects, reorganize data objects, display data objects, modify or annotate data objects, transfer data objects to so-called reports, and the like.

Figure 3:
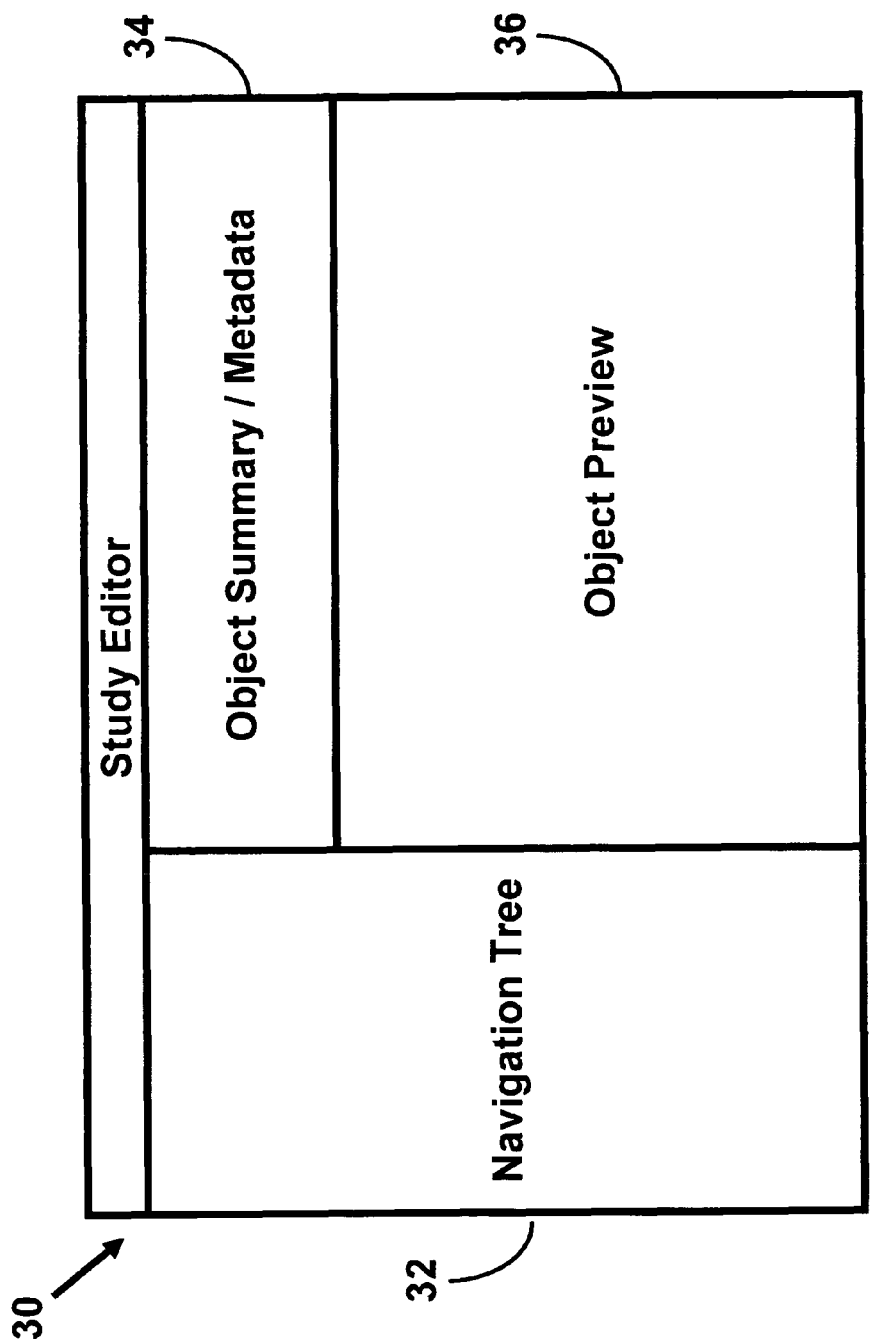
FIG. 3 shows schematically an aspect of an exemplary graphical user interface provided by the metabolic pathway data management system according to the present invention.
Figure 4:
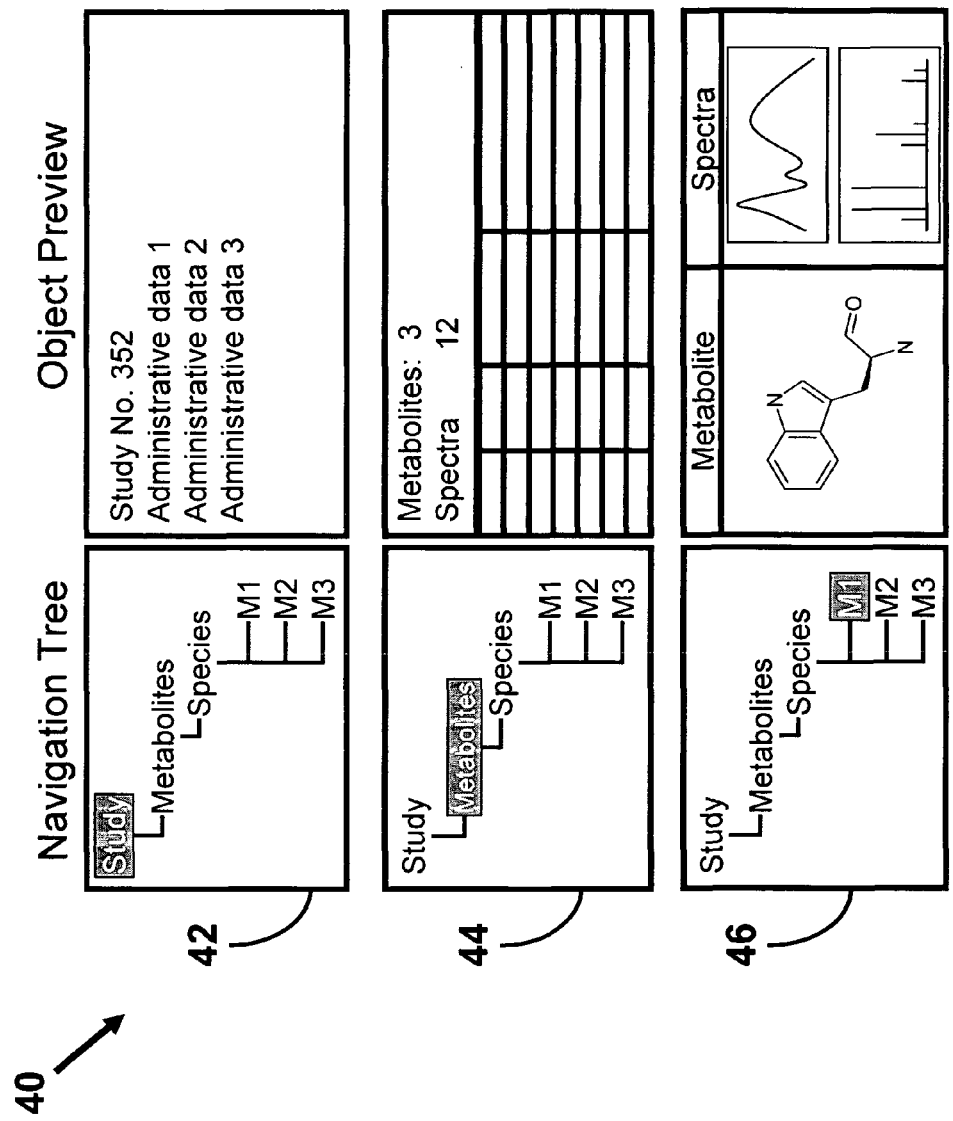
FIG. 4 shows schematically several exemplary details of the graphical user interface of FIG. 3.

FIG. 3 shows a graphical representation of an exemplary graphical representation of a part of the study editor 30 consisting of several frames or windows as provided by the graphical user interface of the MPDMS according to the present invention. The navigation tree 32 in the left part of the main window is the main tool for visualizing given sets of data objects. It displays a tree of currently opened records in a style just like e.g. the Windows Explorer (cf. FIG. 4). The nodes can be collapsed or expanded similar to the procedure in conventional software programs. In addition the file tree contains its own popup menus to enable fast access to node related commands. The tree structure is customizable and allows a simple access to all data objects in a well organized manner. Data objects can be selected in the navigation tree and loaded and displayed within the data object workspace or preview 36. A filter gives the user the ability to reduce the amount of data objects shown in the navigation tree according to different types of filter criteria.

The navigation tree 32 preferably is the primary navigation tool for accessing all data objects stored in the database. On the basis of the "raw" data in the database storage the navigation tree module builds a hierarchical structure, wherein all data a displayed in a user-defined manner. The only imperative container needed for storage of any data object is the "study" the object has to be assigned to. If no study identifier is assigned to a data object, this object cannot be stored in the database. The study tree view represents selected metadata. Preferably, each user may define a personal view, including e.g. the number of levels, the hierarchy, i.e. sequence, of levels. This allows a personalized view of the data, e.g. showing only the results for a certain species, showing only intermediate reports, showing only intermediate reports for a certain species and the like.

Metadata 26 are descriptive pieces of information for study entries, i.e. (data) objects 24. According to the present invention metadata consist of a pair of meta keys and meta values. Meta keys can be e.g. species and gender. The corresponding meta values are mouse, rat, dog and male, female. There are certain cases where previously selected meta values affect the available meta values in another list. For instance, by introducing a dependency between sets of metadata, which may be configured during set-up of metadata lists. The primary requirements are to simplify the input of metadata and to avoid any errors.

The structured presentation and subsequent handling of data objects 24 in the navigation tree 32 according to the present invention is based on the metadata 26 which is attached to every single data object. Structuring metadata may be set as mandatory. If a metadata is declared as mandatory, then a data object cannot be entered into the database if it has no value assigned. User defined structuring metadata may be for instance compound, dosage(s), sample matrix, species, sex of animals, age of animals. These structuring metadata settings propose the given 6 metadata to be assigned to each data object entered into the database for that particular study. The structuring metadata are possible nodes for the navigation tree with customizable order, as shown exemplary in FIG. 4.

Figure 5:
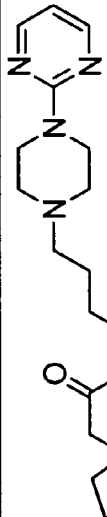
FIG. 5 shows schematically the relation between the data of an exemplary object and its corresponding metadata within the metabolic pathway data management system according to the present invention.
Figure 6:
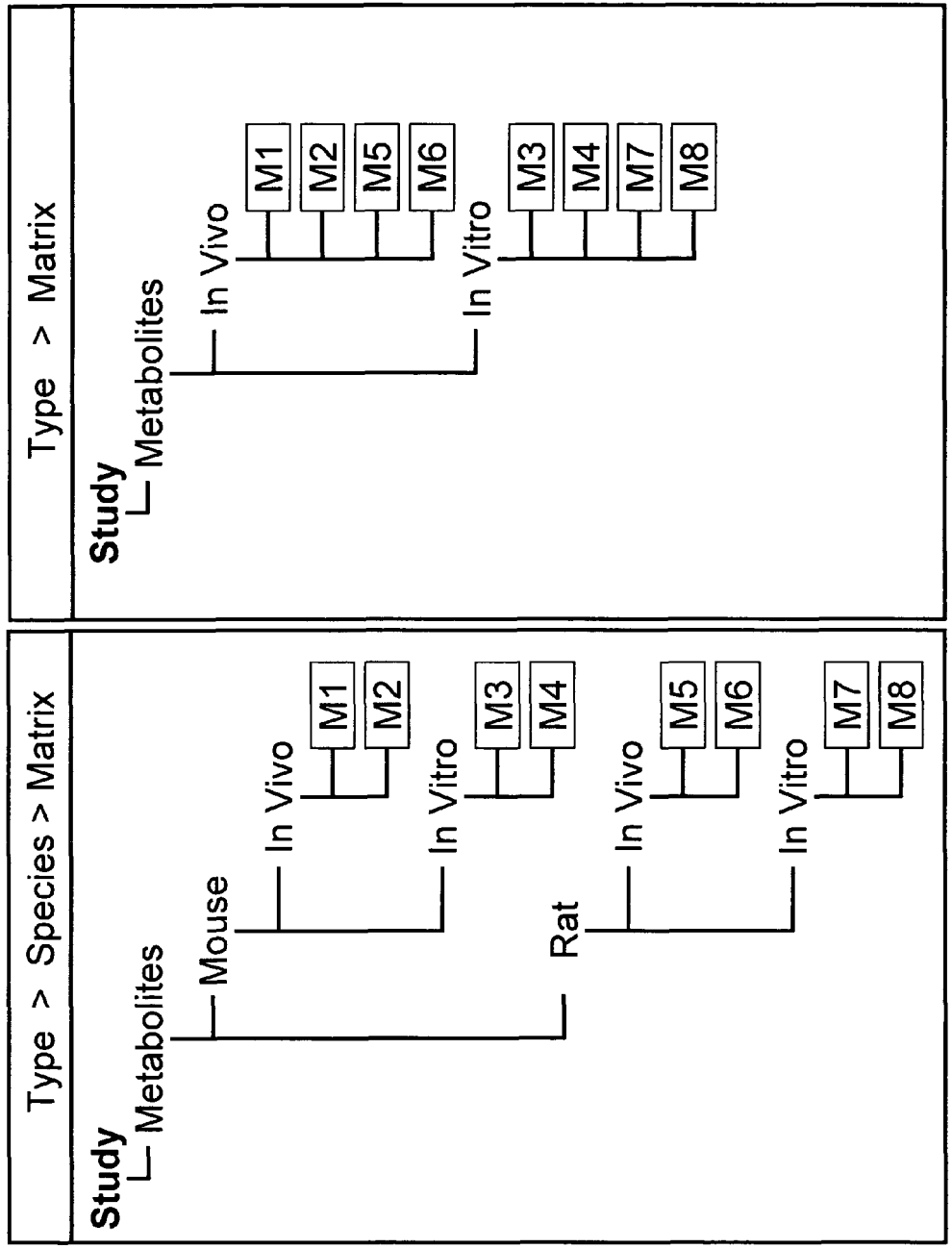
FIG. 6 shows schematically two exemplary hierarchical structures of data objects in navigation trees of the study editor of the metabolic pathway data management system according to the present invention as provided by the graphical user interface thereof.

Each data object may have several metadata that can be used for categorization, as shown in FIG. 5 for the example of a metabolite, including study, species, compound, sex, dosage and sample time. The user must define the organization and representation within a tree view. Different (user specific) tree view settings preferably can be stored and selected from a view menu. To define a new tree view scheme the user selects the metadata that is to be used for categorization and the order in which they shall appear in the tree. FIG. 6 shows on the left hand side a first example of a tree view where the data objects have been organized by type (metabolites), species (mouse, rat), and matrix (in Vivo, in Vitro). On the right hand side of FIG. 6 the data objects have been organized in the order of type, and matrix.

Figure 7:
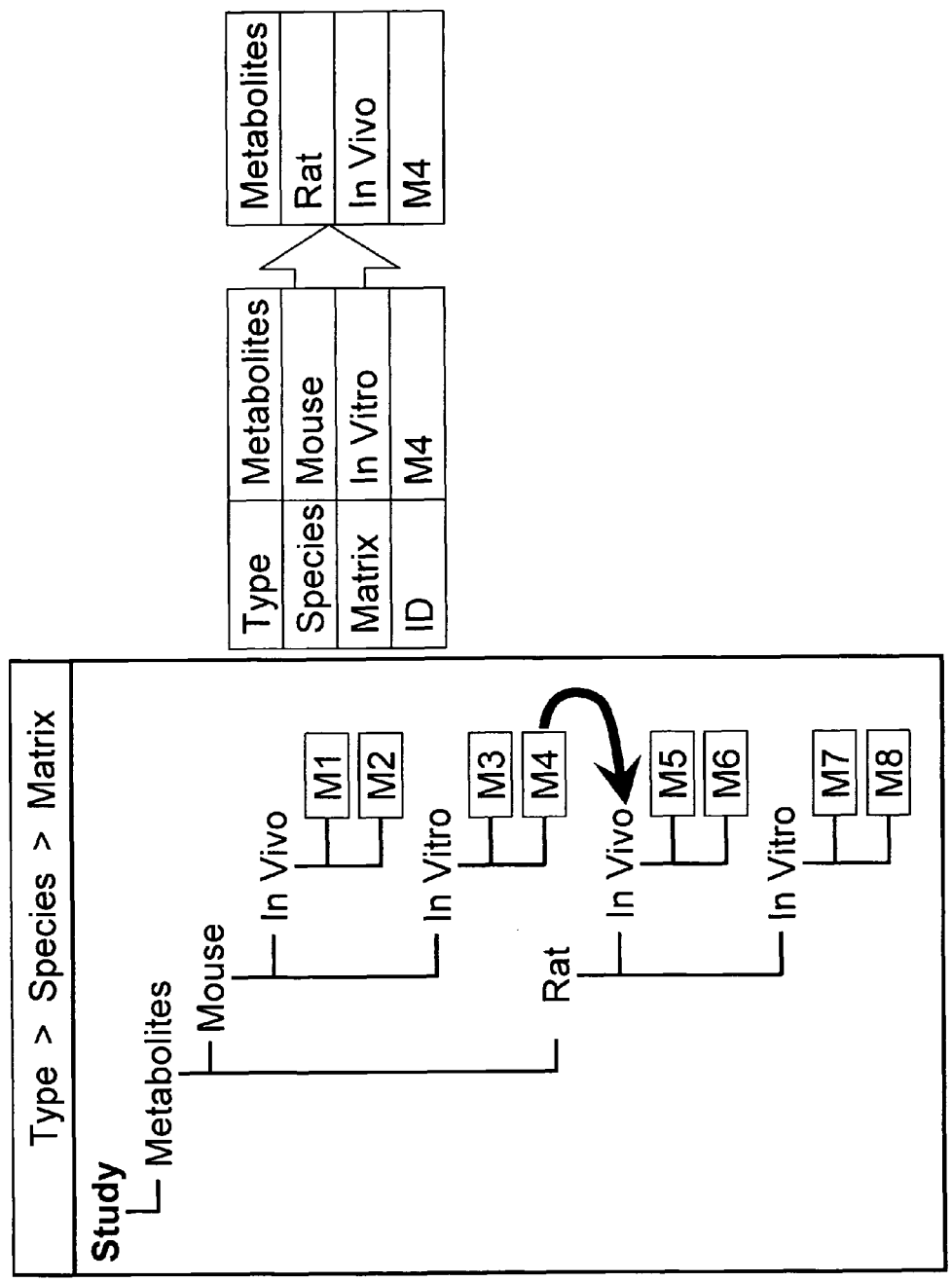
FIG. 7 shows schematically the process of copying/moving one entry in one of the navigation trees of FIG. 6 to another position.

Metadata of data objects that already are stored in the database preferably can be modified by two different mechanisms: (i) defining metadata within the data object properties or (ii) automatic metadata assignment by drag & drop techniques. Data objects to which not all structuring metadata have been assigned remain in an upper level of the navigation tree. Missing metadata can automatically be assigned if such data objects are dragged & dropped to the distinct position in the tree. The metadata values result from the position within the tree. This is shown schematically in FIG. 7.

The scheme shows the effect of moving the object M4 in the folder "Study/Metabolites/Mouse/In Vitro" to another folder, here the In Vivo folder of the Rat. Since in this example two meta keys are affected, namely species and matrix, their corresponding meta values are changed. A similar effect is achieved if data objects are copied from one folder to another. The difference is that the previous metadata are kept, and new metadata are added to the data object. This method can be used to easily reorganize or refine the metadata of data objects or to complete the metadata of data objects with incomplete metadata.

In order to avoid metadata being overwritten or lost it is only allowed to drag & drop objects to a sub folder of the recent object position in the tree. If a metadata is for a metadata that would automatically be assigned by dropping an object to another folder then a warning message will appear. For example if a "Mouse" object is dragged to a "Rat" folder a message shows the user which metadata are affected.

The object summary frame 34 of the study editor (cf. FIG. 1) facilitates a quick overview of the information related to a selected item in the navigation tree 32. Selectable items within the navigation tree are folders, i.e. nodes, or data objects. Preferably, three different types of object summaries are provided depending on the type of the selected item: a study folder, a folder other than a study folder, i.e. a node, or a data object. The object summary frame can be expanded and collapsed.

The selection of a data object within the navigation tree results in the display of its related metadata within the object summary frame. Metadata values can be modified, added or deleted (only for non mandatory values) within this frame.

Data objects selected in the navigation tree can be displayed in the study editor workspace or object preview 36. Due to the unknown number and size of data objects belonging to a study, data objects preferably must be loaded explicitly. A data object can be loaded from the database and displayed in the graphical representation of the study editor by clicking the data object entry.

Depending on the selected part of the navigation tree, the object preview area 36 shows different data. Selecting the top node 42 shows study summary data, selecting a folder 44 shows details about the contained objects. Finally, selecting an object in the tree 46 previews the corresponding data in an internal viewer. The data objects loaded and displayed in the study editor workspace can be of different types, such as OLE objects (Object Linking and Embedding), RTF objects, JCAMP-DX objects, pathway objects and report objects.

For any upload of a data object the user is prompted with a metadata entry window, having the possibility to enter values for the structuring metadata. Metadata can be selected from a predefined value list or entered manually. Predefined value lists help to avoid misspellings and usage of different abbreviations or wording, resulting in a mess of categories.

If mandatory metadata are not entered then the system will refuse to import the object. If the data entry is finished the user can finalize the import by pressing the "Ok" button. Hitting the "Cancel" button exits the metadata entry window without importing the object.

A scientist will certainly produce series of data usually with the same set of metadata to store in the database at a time. To avoid the reentering of metadata for each single data object, the object upload preferably provides a default metadata scheme capability. The metadata scheme is a list of metadata with corresponding values. The users can define, save, load (and later modify) default settings for a file upload.

The system according to the present invention allows defining dependencies of metadata. Dependencies reduce the amount of available values in a secondary metadata list, depending on the selected meta value in a primary list as illustrated in FIG. 8.

Figure 8:
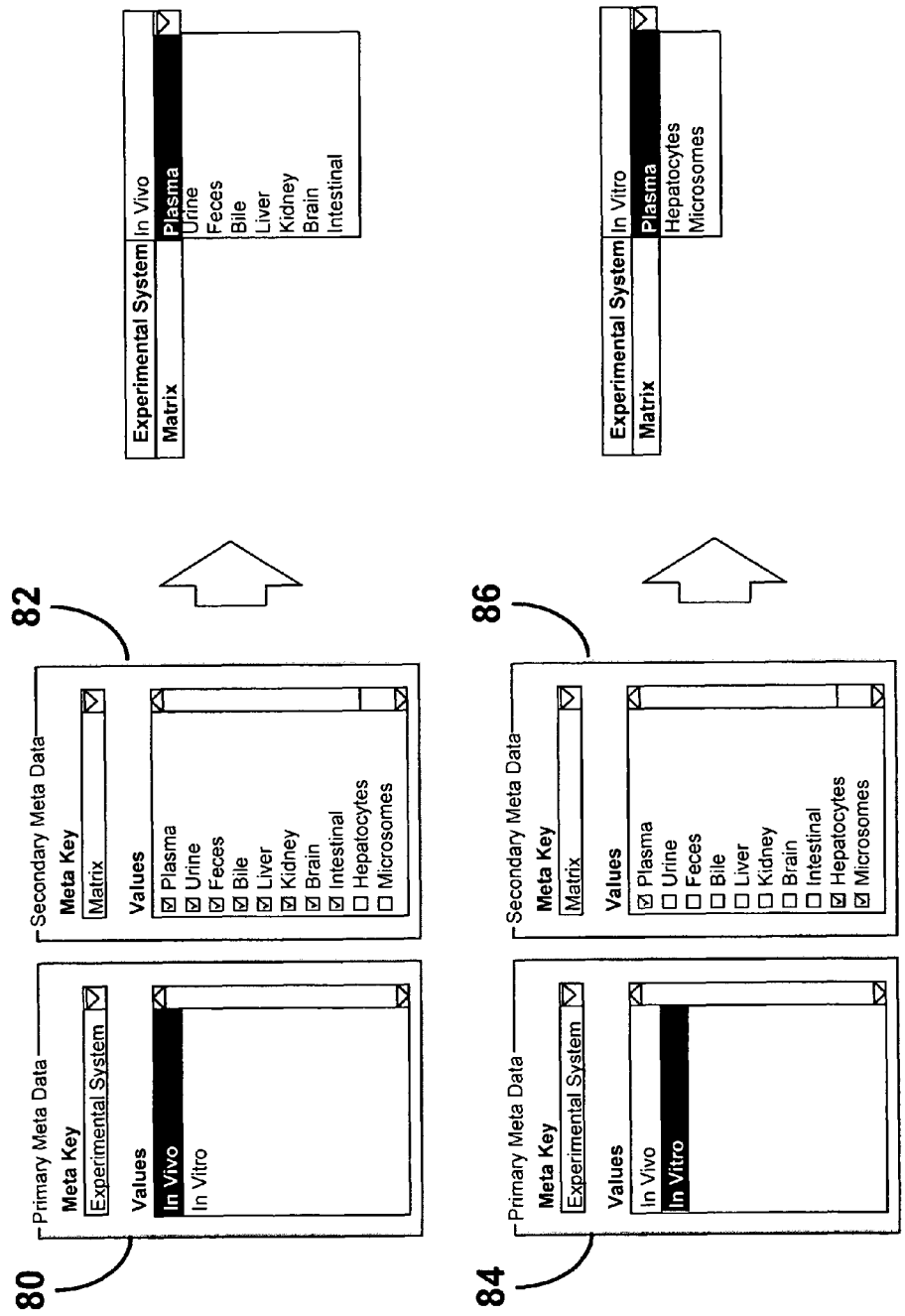
FIG. 8 shows a graphical representation of the interrelationship between primary metadata and secondary metadata within the metabolic pathway data management system according to the present invention.

FIG. 8 shows a dependency of secondary metadata 82 on the primary metadata 80. By selecting the meta value "In Vivo" in the primary metadata section 80, only a restricted set of values is available for "Matrix". The same applies vice versa. The dependency may be defined for any value of the primary metadata, as shown in FIG. 8. By selecting the meta value "In Vitro" 84 in the primary metadata section 80, only a restricted set of values is available for "Matrix". Both dependencies can be defined individually and independent from each other. As shown in the example in FIG. 8, both reduced lists of meta values for the meta key "Matrix" contain the meta value "Plasma". This approach allows administering large sets of meta values consistently in a single list, but avoiding to confront the user with unmanageable amount of values.

An automated upload of instrument data can be performed by specially configured agents, such as described in EP 04 024 280, which is incorporated herein by reference. To this end, a source directory has to be defined, from where the agent automatically transfers files to the MPDMS according to the present invention. The agent is capable of automatically extracting metadata from either the file content, the file name or the folder name. For example: if a file is dropped to the source folder and the first six characters of the filename are "123456" (study ID) then the agent can automatically create a metadata "Study ID=123456".

In addition to the study editor described above the MPDMS according to the present invention further comprises a pathway editor. The pathway editor allows the user to define the contents and the arrangement of metabolites in a metabolic pathway. It incorporates preferably a Microsoft®.NET library for editing schematic diagrams, such as Northwoods GoDiagram™. A diagram, i.e. the graphical representation of a metabolic pathway, consists of generic objects and connections between objects that can be arranged and manipulated graphically.

Figure 9:
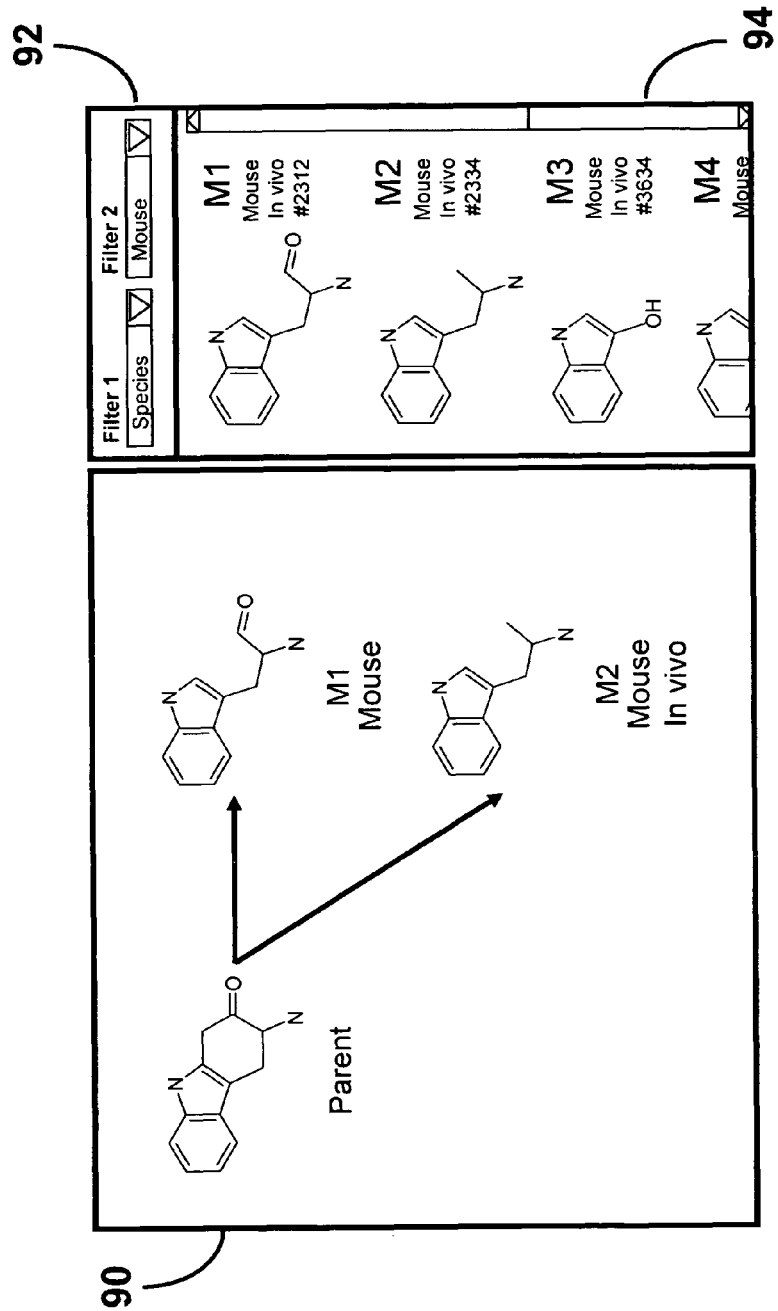
FIG. 9 shows a graphical representation of the pathway editor of the metabolic pathway data management system according to the present invention as provided by the graphical user interface thereof.

The pathway editor is only available for a selected study and can only be started, if a study is open. Only structure data (parent and metabolite structures) of the corresponding study are accessible in the pathway editor. An exemplary pathway editor consists of a graphical representation of the pathway, i.e. the pathway diagram, on the left-hand side and a structure list on the right, such as illustrated in FIG. 9. Both components are preferably divided by a movable splitter that allows changing the size of one component relative to the other. On resize of the entire pathway editor window, the components are resized, preferably, with the structure list maintaining the original size relation and the pathway view is resized according to the window frame.

The pathway diagram 80 displays a graphical frame containing the metabolic path with parent/metabolite structures, connectors, and annotations. The pathway diagram preferably has two views selectable by the corresponding menu entry: (i) a schematic view and (ii) a metabolite view.

Figure 10:
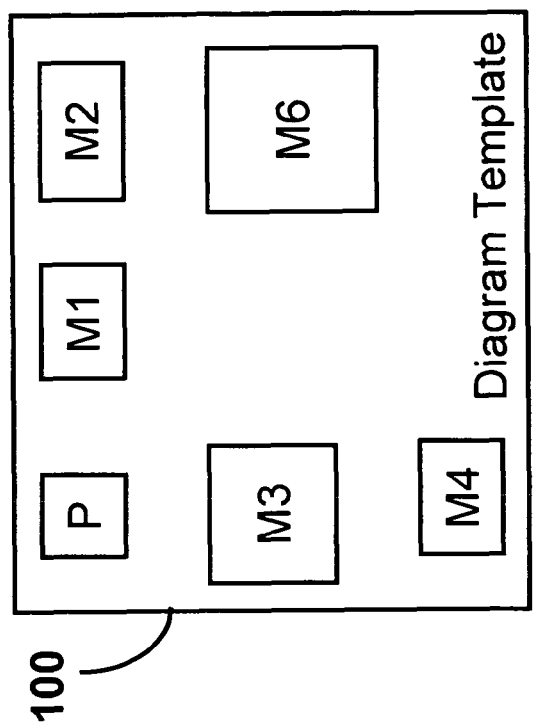
FIG. 10 shows schematically a diagram template provided by the pathway editor of the metabolic pathway data management system according to the present invention.

The schematic view displays objects as boxes instead of contents, as shown in FIG. 10 for the case of a diagram template. The schematic view is designed for an easy and fast arrangement of objects and their connections. Using a schematic view, objects can be inserted and their position can be shifted graphically on the screen. The position, i.e. the actual arrangement, of the objects can be stored and retrieved for later use.

In order to display a full metabolic pathway, the user can switch to the metabolite view as shown in FIG. 9. The metabolite view displays the full content of the objects, i.e. the chemical structures and all data associated with the object selected for display. Moving the mouse over a structure, preferably, causes a hint box with additional information on the structure to be displayed, such as metabolite number, metadata field entries. Each structure object contains a context menu that allows to export the structure to the local file system in Jcamp or MDL Mol file format, or to export the entire set of visible metabolites to MDL SD file format.

A structure box is the container for a metabolite. It includes a structure drawing boundary and optionally additional descriptive fields. Metabolites can be inserted by dragging a metabolite from the metabolite list view 94 or by selecting the corresponding transfer item in the metabolite context menu entry. The user has three possibilities depending on the component underlying the drop position: (i) dropping on an empty part of the pathway diagram leads to the creation of a new structure box and insertion of the selected metabolite into the box; (ii) dropping on an existing empty structure box inserts the selected metabolite into the box; and (iii) dropping on an existing structure box containing a structure entry displays a dialog box asking the user whether to replace the existing structure, to create a new structure box, or to cancel the action.

Only metabolites already existing in the corresponding study can be inserted as described above. New metabolites may be inserted via the menu entry in the same way as uploading a new object in the study editor described above.

Metabolites may have a series of properties that can be viewed by selecting the main menu or context menu entry "Properties". Properties are preferably divided into the following sections: (i) "details", (ii) "molecule", (iii) "metadata", (iv) "connections", and (v) "associated data".

The properties section "details" can include data such as administrative data and details about the metabolite entry, type (i.e. parent or metabolite), metabolite number (i.e. the unique identifier for the metabolite within the study, e.g. M3), a name for the metabolite, an optional description or comment for the metabolite, date and time of creation of the database entry, full name of the user that created the entry, date and time of last change of the database entry and full name of the user that changed the entry on the last access.

The properties section "molecule" can include data such as the molecular formula, e.g. $C24H36N2OCL$, the nominal mass, i.e. the calculated molecular mass of the chemical structure derived from nominal atomic masses including mass differences from residue information, any special conditions applied to the atoms of the structure.

The properties section "metadata" contains a list of predefined metadata for metabolite entries including a mandatory flag, e.g. parent compound number/structure, metabolite, species, sample matrix, in vitro model, study/protocol number or ID, gender, age and the like. The properties section "connections" contains a list of connected metabolites identified via their metabolite number, e.g. M3. And, the properties section "associated data" contains a list of associated (uploaded) chromatograms, spectra, and other data sorted according to the data type, e.g., 1H-NMR spectra, MS spectra, Text files, OLE files and the like.

Connectors are objects that contain the connectivity information that can be assigned to a pair of metabolites. Connectors may be defined on the basis of the graphics library. Connectors may be shifted or their start and end points may be attached to other objects. Open connectors are allowed while working on the pathway arrangement. Connectors are defined by type, size and line width, left/right arrow type. By selecting the context menu item "Insert-Connector", a default connector (arrow) is created on the basis of the default settings for connectors. Connectors can be attached graphically to one or two structure boxes in the pathway.

The metabolite list contains a filter 92 and a list of graphical representations 94 of the chemical structures of the metabolites that are available within the study. The filter preferably contains two dropdown boxes: (i) the field dropdown and (ii) the item dropdown.

The field dropdown allows the user to select the metadata field defined in the metadata fields of the generic structure object that has to be applied to the second dropdown component. The first entry contains a "(none)" entry and acts like the "*" wildcard, i.e. the filter criterion is not applied to the structure list. With "(none)" selected, the second dropdown is disabled. The item dropdown contains all metadata entries (defined via value collections) for the metadata field name selected in the first dropdown box. The dropdown fields are updated when the selection of the field dropdown is changed. The first entry contains a "(none)" entry and acts like the "*" wildcard, i.e. the filter criterion is not applied to the structure list.

Pathways may possess a multitude of properties that can be viewed by selecting the main menu or context menu entry "Properties". The pathway properties preferably are divided into the following sections: (i) details, including administrative data and details about the pathway, a pathway number (i.e. the unique identifier for the pathway), a name for the pathway, an optional description of the pathway, date and time of creation of the database entry, full name of the user that created the entry, date and time of last change of the database entry, full name of the user that changed the entry on the last access; (ii) contents, including the actual number of metabolites available in the pathway, the actual number of connectors available in the pathway, and the actual number of annotations available in the pathway; and (iii) associated data, including a list of associated (uploaded) chromatograms and other data sorted according to the data type, e.g., liquid chromatograms, text files, OLE files, and the like.

The graphical user interface of the present invention allows a graphical creation of a metabolic scheme. To this end, first administrative data has to be defined, e.g. information about the study, sample, and the like, thereafter the parent structure has do be defined, e.g. structures have to be drawn and metadata has to be added, and finally a metabolite object is added. Adding a metabolite object creates a placeholder for a metabolite structure. All inputs are optional. Inputs include metadata, structure, instrumental results (e.g. spectra), connectivity information.

A pathway diagram template stores all information about the actual arrangement of objects in a pathway diagram and their formatting. It is used to easily create a new pathway diagram on the basis of an existing one. The information stored includes metabolite identifiers, e.g. P, M1, M2, positions of metabolites, size of metabolites, general formatting of objects, including fonts, line widths and the like.

Pathway diagram templates do not contain any information about connectivity of metabolites. However, a diagram template may consist only of formatting information, for instance fonts, line widths, etc.; i.e., objects are not mandatory. Diagram templates can be applied to new pathway diagrams. When a new pathway is created, a diagram template may be used as a predefined master. Diagram templates may be stored on server or on local hard disk by selecting the corresponding menu entry.

Each metabolite saved to the database is stored including connectivity information and metadata. Using a pathway diagram template, any existing set of metabolites having one metadata in common with the diagram template may be mapped thereon. FIG. 10 shows an example of a diagram template 100, consisting of a parent P and metabolite positions of the metabolites M1, M2, M3, M4 and M6.

Figure 11:
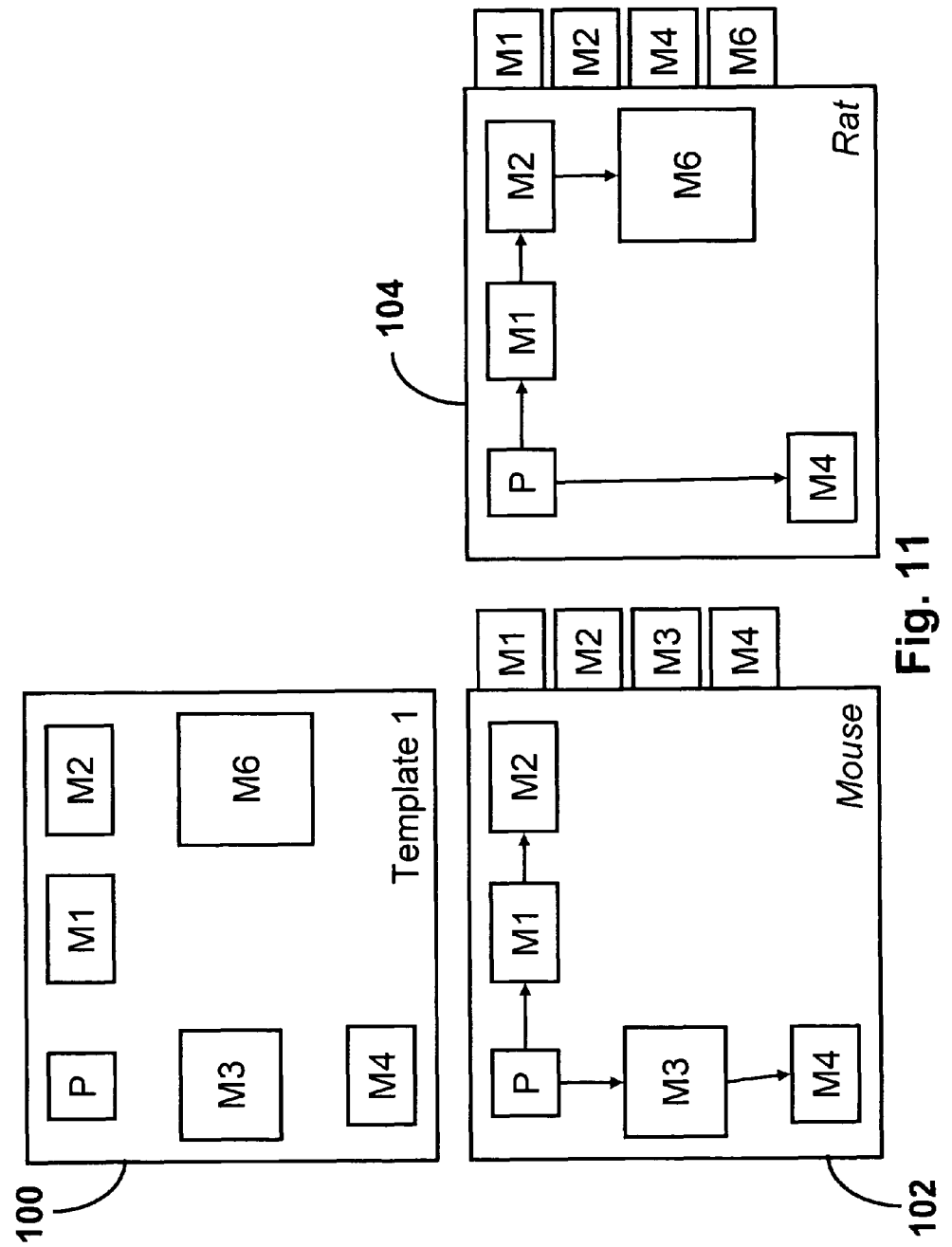
FIG. 11 shows schematically two metabolic pathways resulting from mapping two different sets of metabolites onto the diagram template of FIG. 10.

In order to map a set of metabolites onto the template, the user can select the metadata key and value in the filter. The result of mapping the metabolites M1-M4 found in the mouse (meta key: species, meta value: mouse) onto the template 100 is shown on the lower left side of FIG. 11.

The MDPMS according to the present invention performs the mapping in the following manner. All identical metabolites are transferred to their respective positions. All connectors are created according to the connectivity information of the metabolite. Metabolite M6, which is not available in the metabolite set of "Mouse", is left out of the scheme. Mapping another set of metabolites (e.g, M1, M2, M4, M6 found in the "Rat") onto the Diagram Template 100, results in the metabolic pathway shown on the lower right side of FIG. 11. In this case, metabolite M3, which has not been detected in the "Rat", is left out, the position of M4 is not changed, and M6 appears at the respective position.

Figure 12:
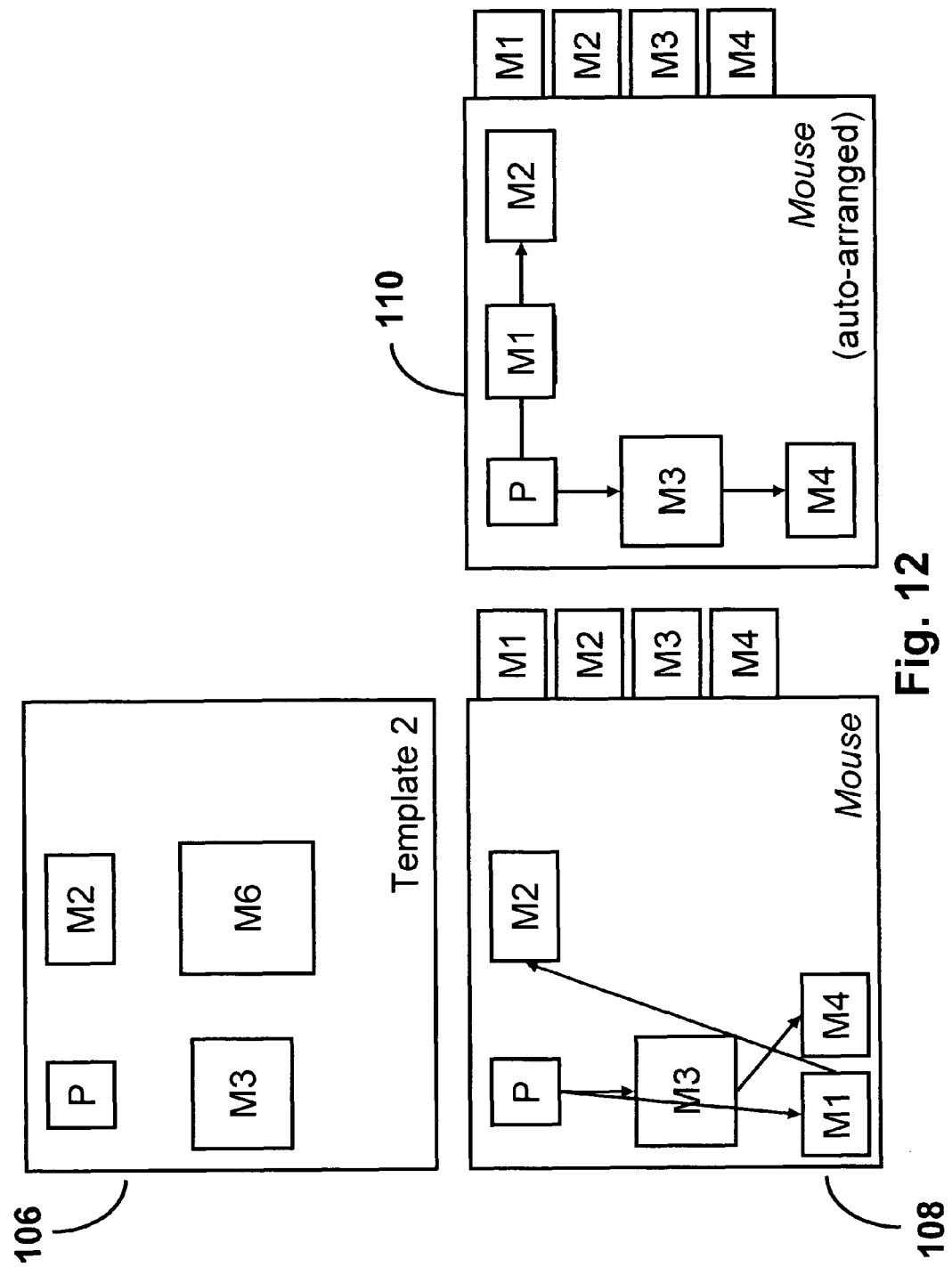
FIG. 12 shows schematically a metabolic pathway in two different forms resulting from mapping a first set of metabolites onto a further diagram template.
Figure 13:
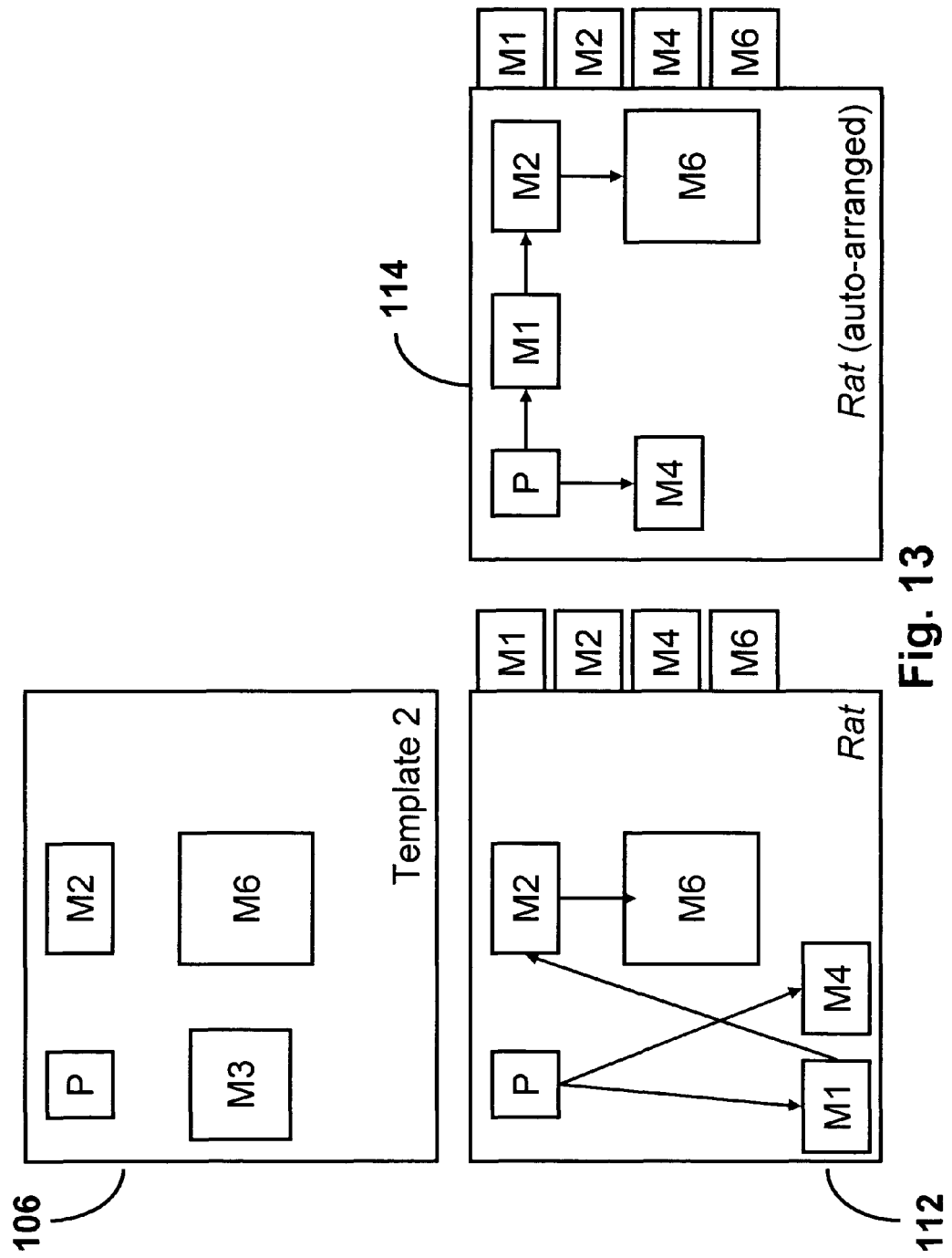
FIG. 13 shows schematically a metabolic pathway in two different forms resulting from mapping a second set of metabolites onto the further diagram template of FIG. 12.

The mapping of metabolite information onto an incomplete pathway diagram template, i.e. a template that does not contain a position for a metabolite existing in a certain set, is handled differently. Such an incomplete template 106 is shown in FIG. 12. Mapping the "Mouse" metabolites (M1, M2, M3, M4) onto this template will lead to the following behavior. The metabolites existing in both the template and the set of metabolites of the "Mouse" are mapped onto their respective positions. Metabolites from the set, which have no distinct definition in the template, are arranged sequentially in the lower left corner of the pathway. The connectors are created, although this may lead to unfavorable arrangement. In this case, the user may rearrange the positions of the metabolites manually, whereby the connector stay attached to their metabolite. Another way is to use an auto-arrange option according to the present invention to clean-up the display. The results are shown in FIG. 12 for the "Mouse" and in FIG. 13 for the "Rat" including the metabolites M1, M2, M4 and M6.

Pathways may be automatically arranged in the schematic view by a so-called layered-digraph auto-layout. The layered-digraph auto-layout routines works as follows: the nodes in the graph are placed into layers such that all of a node's predecessors are in a higher layer and all of a node's successors are in a lower layer; the routine then heuristically permutes the orders of each node within a layer such that the total number of link-crossings is reduced. Finally, the routine adjusts the positions of each node within a layer to reduce the number of bends required by the links. In order to layout arbitrary directed graphs, the layered-digraph routine removes cycles from graphs by temporarily reversing some links.

A pathway diagram template 100, 106 may be used to create a default pathway for a study. As mentioned before, each pathway keeps its own information about the position of metabolites. Mapping a pathway onto a template allows to visualize the differences between pathways. However, until the pathway is not stored, it will keep its individual arrangement. By storing the pathway after mapping, the template is transferred to the pathway and kept with the actual arrangement. On the other hand, each created pathway may serve as basis for a template. By selecting the "Save As Template" menu entry, the arrangement of parent and metabolite structures of the actual pathway may be stored as a diagram template and made available in the study. Preferably, a pathway diagram may be exported as an image to the local file system. The available formats are MDL Mol Files, Windows Bitmap, JPEG Image, Tagged Image File, Window Meta File. In addition, it can be sent to an ELN system as an individual entry.

The invention claimed is:

1. A metabolic pathway data management system in a distributed communication network comprising:
   at least one application server running a metabolic pathway data management server application;
   at least one client workstation running a metabolic pathway data management client application in communication with the at least one application server via the distributed communication network; and
   at least one database for storing data in communication with the at least one application server via the distributed communication network,
   wherein said metabolic pathway data management client application provides a graphical user interface allowing for the input of information about metabolites of a metabolic pathway of interest, including connectors between the metabolites,
   the graphical user interface providing at least one pathway diagram template containing information about an arrangement of metabolites and allowing for a mapping of the metabolites of the metabolic pathway of interest onto the pathway diagram template by arranging all the metabolites of the metabolic pathway of interest that are identical to the metabolites of the pathway diagram template at a position of the respective metabolite of the pathway diagram template, displaying the connectors between the metabolites of the metabolic pathway of interest, and automatically re-arranging the metabolites of the metabolic pathway of interest.

2. The metabolic pathway data management system of claim 1, wherein the data comprises data objects classified on the basis of their metadata.

3. The metabolic pathway data management system of claim 1, wherein the graphical user interface includes a study editor that provides a navigation tree having a user-defined structure.

4. The metabolic pathway data management system of claim 3, wherein the study editor allows the user to store the data objects in the database, navigate within the data objects in the database, categorize the data objects, reorganize the data objects, display the data objects, modify or annotate the data objects, and transfer the data objects to reports.

5. The metabolic pathway data management system of claim 1, wherein the data comprises metadata consisting of meta keys and meta values.

6. The metabolic pathway data management system of claim 1, wherein the data comprises metadata of data objects stored in the database that can be modified by an automatic metadata assignment by means of drag & drop techniques.

7. The metabolic pathway data management system of claim 1, wherein the data comprises metadata and dependencies of metadata can be defined.

8. The metabolic pathway data management system of claim 1, wherein the graphical user interface includes a pathway editor comprising a pathway diagram and a structure list.

9. The metabolic pathway data management system of claim 8, wherein the pathway editor provides a schematic view and a metabolite view displaying the full content of the objects including chemical structure images associated with the objects.

10. The metabolic pathway data management system of claim 9, wherein the automatics re-arrangement occurs in the schematic view.

11. The metabolic pathway data management system of claim 10, wherein the automatic re-arrangement is performed by a layered-digraph auto layout.

12. The metabolic pathway data management system of claim 8, wherein the pathway editor provides (i) a schematic view in which a first graphical depiction of the metabolic pathway is displayed as a collection of generic images representing a parent compound and the metabolites of the metabolic pathway; and (ii) a metabolite view in which a second graphical depiction of the metabolic pathway is displayed as a collection of chemical structure images representing the parent compound and the metabolites.

13. The metabolic pathway data management system of claim 12, wherein the generic images are in the form of boxes representing the parent compound and the metabolites of the metabolic pathway.

14. The metabolic pathway data management system of claim 12, wherein the schematic view allows the user to insert the generic images into the first graphical depiction of the metabolic pathway.

15. The metabolic pathway data management system of claim 12, wherein the schematic view allows the user to edit the metabolic pathway by inserting or rearranging the generic images within the first graphical depiction of the metabolic pathway.

16. The metabolic pathway data management system of claim 8, wherein the pathway editor and the structure list are separated by a movable splitter that allows changing the size of the pathway editor relative to the structure list.

17. The metabolic pathway data management system of claim 1, wherein the pathway diagram template can be used for creating a new pathway.

18. The metabolic pathway data management system of claim 1, wherein the data comprises a project, a study, an object, and a metadata data type.

19. The metabolic pathway data management system of claim 1, wherein the graphical user interface comprises a study editor and a pathway editor.

20. The metabolic pathway data management system of claim 19, wherein the study editor as a main interface for the user provides a navigation tree allowing a classification of the data objects in a tree format according to their metadata.

21. The metabolic pathway data management system of claim 19, wherein the pathway editor allows the user to define the contents and the arrangement of metabolites in a metabolic pathway.

* * * * *